US008901104B2

(12) United States Patent
Nilsson et al.

(10) Patent No.: US 8,901,104 B2
(45) Date of Patent: *Dec. 2, 2014

(54) USE OF DEXTRAN SULFATE

(71) Applicant: TX Medic AB, Viken (SE)

(72) Inventors: Bo Nilsson, Uppsala (SE); Olle Korsgren, Uppsala (SE)

(73) Assignee: TX Medic AB, Viken (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/099,518

(22) Filed: Dec. 6, 2013

(65) Prior Publication Data

US 2014/0094435 A1    Apr. 3, 2014

Related U.S. Application Data

(63) Continuation of application No. 10/535,876, filed as application No. PCT/SE03/01830 on Nov. 26, 2003, now Pat. No. 8,629,123.

(30) Foreign Application Priority Data

Nov. 28, 2002  (SE) ...................................... 0203526

(51) Int. Cl.
    *A61K 31/721*    (2006.01)
    *A61K 35/39*     (2006.01)
    *A61K 31/737*    (2006.01)

(52) U.S. Cl.
    CPC ............... *A61K 31/737* (2013.01); *A61K 35/39* (2013.01); *A61K 31/721* (2013.01)
    USPC .............................. 514/59; 514/54; 536/112

(58) Field of Classification Search
    CPC . A61K 31/721; A61K 31/715; A61K 9/0019; A61K 9/08
    USPC ...................................... 514/59, 54; 536/112
    See application file for complete search history.

(56) References Cited

U.S. PATENT DOCUMENTS 5,736,506 A    4/1998  Naka
5,849,689 A    12/1998 Chamow et al.

OTHER PUBLICATIONS

Brauer R B, et al., "The contribution of terminal complement components to acute and hyperacute allograft rejection in the rat", Transplantation, vol. 59, No. 2, pp. 288-293 (1995).
Bennet W, et al., "Damage to porcine islets of Langerhans after exposure to human blood in vitro, or after intraportal transplantation to cynomologus monkeys: protective effects of sCR1 and heparin", Transplantation, vol. 69, No. 5, pp. 711-719 (2000).
Nakano M, et al., "Hepatocyte growth factor is essential for amelioration of hyperglycemia in streptozotocin-induced diabetic mice receiving a marginal mass of intrahepatic islet grafts", Transplantation, vol. 69, No. 2, pp. 214-221 (2000).
Thomas H, et al., "Sulfonated dextran inhibits complement activation and complement-dependent cytotoxicity in an in vitro model of hyperacute xenograft rejection", Mol Immunol, vol. 33, No. 7-8, pp. 643-648 (1996).
Shapiro A M, et al., "Islet transplantation in seven patients with type 1 diabetes mellitus using a glucocorticoid-free immunosuppressive regimen", N Engl J Med, vol. 343, No. 4, pp. 230-238 (2000).
Fiorante P, et al., "Low molecular weight dextran sulfate prevents complement activation and delays hyperacute rejection in pig-to-human xenotransplantation models", Xenotransplantation, vol. 8, No. 1, pp. 24-35, (2001).
Pratt J R, et al., "Effects of complement inhibition with soluble complement receptor-1 on vascular injury and inflammation during renal allograft rejection in the rat", Am J Pathol, vol. 149, No. 6, pp. 2055-2066, (1996) (Abstract).
Carroll M C, and Fischer M B, "Complement and the immune response", Curr Opin Immunol, vol. 9, No. 1, pp. 64-69 (1997) (Abstract).
Cantarovich D, et al., "Rapid failure of pig islet transplantation in non human primates", Xenotransplantation, vol. 9, No. 1, pp. 25-35 (2002) (Abstract).
Buhler L, et al., "Adult porcine islet transplantation in baboons treated with conventional immunosuppression or a non-myeloablative regimen and CD154 blockade", Xenotransplantation, vol. 9, No. 1, pp. 3-13 (2002) (Abstract).
Bennet W, et al., "Incompatibility between human blood and isolated islets of Langerhans: a finding with implications for clinical intraportal islet transplantation?", Diabetes, vol. 48, No. 10, pp. 1907-1914 (1999).
Ryan E A, et al., "Clinical outcomes and insulin secretion after islet transplantation with the Edmonton protocol", Diabetes, vol. 50, No. 4, pp. 710-719 (2001).
Wuillemin W A, et al., "Potentiation of C1 inhibitor by glycosaminoglycans: dextran sulfate species are effective inhibitors of in vitro complement activation in plasma", J Immunol, vol. 159, No. 4, pp. 1953-1960 (1997).
Babcock et al, Immunology, 33(6):925-929 (1977).
Zioncheck et al, "Sulfated Oligosaccharides Promote Hepatocyte Growth Factor Association and Govern its Mitogenic Activity", Journal of Biological Chemistry, 270(28):16871-78 (1995).
Kaibori et al, "Stimulation of liver regeneration and function after partial hepatectomy in cirrhotic rats by continuous infusion of recombinant human hepatocyte growth factor", Journal of Heptatology, 27:381-390 (1997).

*Primary Examiner* — Shaojia Anna Jiang
*Assistant Examiner* — Michael C Henry
(74) *Attorney, Agent, or Firm* — Porter Wright Morris & Arthur LLP

(57) ABSTRACT

A method of inhibiting Instant Blood-Mediated Inflammatory Reaction (IBMIR) in a patient, comprises administering a therapeutically effective amount of dextran sulfate, or a pharmaceutically acceptable salt thereof. A method of inhibiting morphological disruption of a transplanted cell transplant in a patient comprises administering a therapeutically effective amount of dextran sulfate, or a pharmaceutically acceptable salt thereof, to a patient. The dextran sulfate, or said pharmaceutically acceptable salt thereof, has an average molecular weight of less than 20,000 Da and an average sulphur content in a range of 10 to 25%, and the inhibition comprises administering said therapeutically effective amount of said dextran sulfate, or said pharmaceutically acceptable salt thereof, resulting in a concentration of said dextran sulfate, or said pharmaceutically acceptable salt thereof, in the blood of said patient of less than 5 mg/ml.

28 Claims, 6 Drawing Sheets

US 8,901,104 B2

USE OF DEXTRAN SULFATE

RELATED APPLICATIONS

This application is a continuation of U.S. Ser. No. 10/535,875 filed Jan. 9, 2006, which is a 371 of PCT/SE2003/001830 filed Nov. 26, 2003.

TECHNICAL FIELD

The present invention refers to new use of dextran sulfate.

BACKGROUND

Today, about 10 million of people worldwide suffer from type I diabetes, which is also referred to as insulin-dependent diabetes mellitus. However, the number of affected people is estimated to increase dramatically and may affect as many as 25 million by 2010. Presently, research is conducted for trying to achieve permanent normoglycemia in patients with type I diabetes by introducing insulin-producing β-cells. The two main procedures have been transplantation of either vascularized pancreatic grafts or isolated islets of Langerhans. Although some success has been obtained with vascularized grafts (whole pancreas) problems still remain mainly due to the surgical risk and the post-operative complications. In addition, there is also a problem with shortage of suitable pancreatic graft donors. By contrast, transplantation of isolated pancreatic islets is conventionally performed by injecting the islets transhepatically into the portal vein, whereby the islets embolize in the portal tree of the liver.

A novel protocol for islet allotransplantation that was recently introduced by Shapiro and coworkers [1] will undoubtedly be beneficial to a number of patients with type I diabetes. However, even with this new approach, it has turned out that transplantation of islets from a single donor pancreas is not sufficient to produce normoglycemia in a patient [2]. As a result, the supply of human islets is expected to become a limiting factor in the treatment. Alternative sources of insulin-producing cells will then have to be found. One option is to use islets prepared from animal tissue, with islets from pigs being the chief candidate.

One of the main obstacles to be resolved before islet xenotransplantation becomes possible is the injurious inflammatory reaction that porcine islets elicit when exposed to fresh human blood in vitro and in vivo [3]. Also, human islets induce an injurious inflammatory reaction when exposed to ABO-matched blood of the patient at the time of intraportal transplantation [4]. The inflammatory reaction is characterized by a rapid consumption and activation of platelets, which adhere to the islet surface promoting activation of both the coagulation and complement cascades. In addition, the islets become embedded in clots and infiltrated by CD11b+ leukocytes, which all together results in a destruction of the morphology of the cells and loss of normoglycemia of the patients [3-4]. Furthermore, the inflammation may accelerate the succeeding cell-mediated specific immune response in a later phase [5-8]. Hence, inhibition of Instant Blood-Mediated Inflammatory Reaction (IBMIR), as the injurious inflammatory reaction is called appears to be critical to the success of islet allotransplantation and xenotransplantation.

Two recent studies by Buheler et al. [5] and Cantarovich et al. [6] have demonstrated that adult porcine islets are immediately destroyed when transplanted intraportally into the liver of non-human primates even under conditions of extensive conventional prior art immunosuppression. In these studies, the authors concluded that a powerful innate immune response, IBMIR, which is not affected by immunosuppressive drugs, is involved in the destruction of the xenogeneic islets.

Fiorante et al. have studied the use of dextran sulfate in preventing hyperacute rejection (HAR) of vascularized discordant xenografts [9]. Pig lungs perfused with citrate-anticoagulated human blood experienced HAR after 30 min in the xenotransplantation model. However, addition of dextran sulfate at 2 mg/ml prolonged lung survival to about 200 min. HAR of vascularized whole organs is mediated through the action of antibodies in the human blood, which identify and bind to exposed antigens on the endothelial cells of the blood vessels of the transplanted organs. This antibody-mediated HAR reaction is enhanced by components of the complement system [8, 10, 11]. Since dextran sulfate is also known to inhibit complement activation [9, 12], the prolonged lung survival when using dextran sulfate in the used xenotransplantation model is believed to derive from this anti-complement effect of dextran sulfate.

Nakano and coworkers have transplanted isolated syngeneic islets into livers of STZ-induced diabetic mice in order to investigate the roll of hepatocyte growth factor (HGF) in amelioration of hyperglycemia [13]. Dextran sulfate is known to enhance the effect of HGF and consequently HGF was administered intraperitoneally in the recipient mice in conjunction with dextran sulfate. Such administration produced normoglycemia in all mice under investigation. Also administration of dextran sulfate alone showed some beneficial effect in a few mice, but not when the renal subcapsular space was the site of islet transplantation. Additional anti-HGF antibody treatment to the dextran sulfate administered mice totally abolished the beneficial effect of dextran sulfate, indicating that the effect of dextran sulfate in this model of allogeneic islet transplantation in mice is mediated via endogenous HGF.

Thomas et al. [14] have demonstrated that soluble dextran derivates inhibit complement activation and complement mediated damage in vitro. Porcine aortic endothelial cells incubated in human serum resulted in complement consumption and deposition of activated fragments C3, C5 and of the membrane attack complex C5b-9 on the endothelial cells. Addition of 25 mg/ml of CMDB25 dextran sulfate inhibited complement activation and cytolytic complex deposition on the cells. Native dextran had no such an effect.

SUMMARY

The present invention overcomes these and other drawbacks of the prior art arrangements.

It is a general object of the present invention to provide treatment for Instant Blood-Mediated Inflammatory Reaction (IBMIR).

It is another object of the invention to provide treatment for morphological disruption of cell transplants caused by IBMIR.

Yet another object of the invention is to provide treatment for graft-rejection of cell transplants caused by IBMIR.

These and other objects are met by the invention as defined by the accompanying patent claims.

Briefly, the present invention involves the use of dextran sulfate, and derivates thereof, for treatment of Instant Blood-Mediated Inflammatory Reaction (IBMIR). This newly characterized form of inflammation is triggered when cells or cell clusters are exposed to foreign blood in vitro and in vivo. A very important example of IBMIR is when allogeneic or xenogeneic cell transplants are transplanted into the body of a recipient mammalian, especially human, patient. IBMIR will then lead to morphological disruption and destruction of the transplanted cells or cell clusters, as manifested in loss of structure and form. Furthermore, IBMIR also generally results in graft-rejection of cell transplants.

Administration of dextran sulfate, or derivates thereof, abrogates the deleterious effect of IBMIR and effectively prevents graft-rejection and the morphological disruption of the cell transplants. The dextran sulfate according to the invention may have a molecular weight from low molecular weight dextran sulfate (LMW-DS), e.g. from a few hundred or thousand Dalton (Da), to high molecular weight dextran sulfate (HMW-DS), generally with a molecular weight over 500 000 Da, e.g. >1 000 000 Da. The advantageous effect of dextran sulfate is especially prominent for LMW-DS, but positive effect is also seen by administration of dextran sulfate with a higher molecular weight. The advantageous effect of larger dextran sulfate molecules on IBMIR according to the invention may be enhanced by increasing the sulfur content, i.e. the number of sulfate groups per glucosyl residue in the dextran chain. LMW-DS generally has an average molecular weight of below 20 000 Da, such as below 10 000 Da and e.g. about 5 000 Da. The average sulfur content for LMW-DS may be about 10 to 25%, such as 15 to 20%, corresponding to about two sulfate groups per glucosyl residue. For dextran sulfate with an average molecular weight higher than 20 000 Da, a larger sulfur content could be employed.

Dextran sulfate, and derivates thereof, may be administered for systemic delivery to the site of IBMIR or cell transplantation, or may be administered for delivery directly (locally) to that site. Thus, in accordance with the invention, dextran sulfate, and derivates thereof, may be administered orally, intravenously, intraperitoneally, subcutaneously, buccally, rectally, dermally, nasally, tracheally, bronchially, topically, by any other patenteral route or via inhalation, in the form of a pharmaceutical preparation comprising the active ingredient in a pharmaceutically acceptable dosage form.

In therapeutic treatment of mammals, and especially humans, dextran sulfate and derivates thereof, may be administered alone, but will generally be administered as a pharmaceutical formulation in admixture with a pharmaceutically acceptable adjuvant, diluent or carrier, which may be selected with due regard to the intended route of administration and standard pharmaceutical practice.

The amounts of dextran sulfate, or derivates thereof, in the formulation will depend on the severity of the condition and on the patient to be treated, as well as the actual formulation and administration route employed, and may be determined non-inventively by the skilled person. The concentration of administered dextran sulfate, or derivates thereof, according to the present invention should not be too high in order to minimize any side effects associated with dextran sulfate. In most clinical situations suitable doses of dextran sulfate, or derivates thereof, in the therapeutic and/or prophylactic treatment of mammalian, especially human, patients are those that give a mean blood concentration below 5 mg/ml, probably less than 2 mg/ml and especially less than 1 mg/ml. A preferred concentration range is between 0.01 mg/ml and 1 mg/ml dextran sulfate, such as more than 0.05 mg/ml, more than 0.08 mg/ml or more than 0.1 mg/ml and/or less than 0.8 mg/ml, less than 0.6 mg/ml, less than 0.4 mg/ml or less than 0.2 mg/ml, e.g. within the concentration range of 0.01 mg/ml and 0.2 mg/ml and/or 0.05 mg/ml and 0.2 mg/ml.

The dextran sulfate according to the present invention is especially suitable for preventing graft-rejection of insulin-producing β-cells transplanted into patients suffering from type I diabetes. In such patients, islets of Langerhans from other humans or mammals, preferably porcine islets, may be transplanted by injecting the islets into the portal vein of the patients. However, once the islets are exposed to the blood of the patient IBMIR is triggered and the insulin regulating functionality of the islets will be destroyed and the islets will be rejected. Therefore, a therapeutic concentration of dextran sulfate, or derivates thereof, is preferably attained, at least locally, at the site of transplantation, once transplantation of the cells or cell clusters is performed. This may be obtained by administrating the dextran sulfate prior the actual transplantation. Alternatively, the islets may be injected dissolved in a solution comprising dextran sulfate according to the present invention, in order to inhibit IBMIR and prevent any destruction of rejection of the islets, making normoglycemia in the patients possible. The concentration of dextran sulfate in such a cell and dextran sulfate solution is preferably high enough, so that a therapeutic concentration of dextran sulfate, i.e. preferably less than 5 mg/ml, more preferably 0.01 mg/ml to 1.0 mg/ml, and especially 0.01 mg/ml to 0.2 mg/ml, can be obtained, at least locally, in the site of transplantation for the first hours following transplantation. The dextran sulfate will then diffuse from the site of transplantation lowering the local dextran sulfate concentration. In some applications, no extra dextran sulfate is needed to inhibit IBMIR, morphological disruption and/or graft-rejection of the cell transplants, since a therapeutic concentration of dextran sulfate is probably only needed for the first 24-48 hours after transplantation. However, whenever required, additional dextran sulfate may be added, e.g. intravenously, intraperitoneally, or by some other administration route. As a person skilled in the art understands, administration of a dextran sulfate solution comprising the cells or cell clusters to be administered may also be combined with administration of dextran sulfate, or derivates thereof, prior the actual transplantation.

Dextran sulfate, and derivates thereof, may also be combined with other therapeutic agents that are useful in the treatment of graft-rejection of transplanted tissue. Suitable, but not limiting, examples of such immunosuppressive agents that may be used together with dextran sulfate for treatment of graft-rejection are cyclosporin, tacrolimus, corticosteroids, rapamycin (sirolimus) and mycophenolate mofetil. Administration of dextran sulfate according to the present invention may also be coordinated with administration of anti-TF antibodies and/or site-inactivated factor VIIa, which also have some functionality in inhibiting IBMIR.

SHORT DESCRIPTION OF THE DRAWINGS

The invention together with further objects and advantages thereof, may best be understood by making reference to the following description taken together with the accompanying drawings, in which.

DETAILED DESCRIPTION

Figure 1:
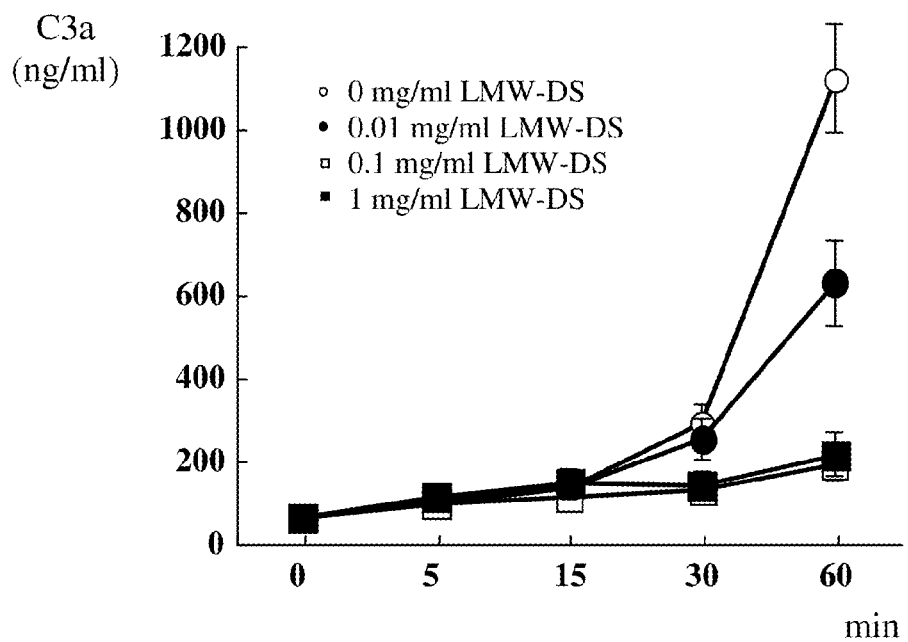
FIG. 1 is a diagram illustrating the effect of LMW-DS on the generation of C3a during perfusion of porcine islets with human blood.

The present invention generally refers to the new surprising effect of dextran sulfate on Instant Blood-Mediated Inflammatory Reaction (IBMIR), and morphological disruption and graft-rejection of cell transplants caused by IBMIR.

IBMIR is a relatively newly identified inflammatory reaction triggered by the exposure or contact of cells or cell clusters with foreign blood. The IBMIR is characterized by expression of tissue factor on the cells, which triggers a local generation of thrombin. Subsequently, activated platelets adhere to the cell surface promoting activation of both the coagulation and complement systems. In addition, leukocytes are recruited and infiltrate the cells. These effects together cause a disruption and destruction of the cell morphology within the first few hours after contact with the foreign blood. IBMIR also accelerates the subsequent cell-mediated specific immune response in a later phase.

A very important example of IBMIR is when cells or cell clusters are transplanted into a body of preferably a mammalian, and especially human, patient. Upon contact with the blood of the recipient patient, the cells trigger IBMIR, which results in disruption of the cell morphology and generally graft-rejection of the cell transplant. IBMIR has been detected both in allogeneic cell transplantation, where cells from a donor with ABO-matched blood are transplanted into a patient, and in xenogeneic cell transplantation, including pig-to-monkey and pig-to-human xenotransplantation of cells and/or cell clusters.

The expression "cell transplant" generally refers, in the present invention, to a single cell, several single cells or a cluster of many cells transplanted into a recipient body of, preferably, a mammalian, and especially, a human patient. Also larger cell clusters of non-vascularized tissues are comprised in the expression cell transplant, as used herein. An example of cell transplants according to the present invention are allogeneic or xenogeneic islets of Langerhans transplanted into the portal vein of the liver of patients suffering from type I diabetes. A further example, may be transplantation of embryonic xenogeneic neural tissue/cells in the striatum of patients with Parkinson's disease.

As was briefly discussed in the background section, a promising procedure for obtaining normoglycemia in patients with type I diabetes is to transplant insulin-producing β-cells e.g. into the portal vein. Suitable insulin-producing cells, e.g. in the form of islets of Langerhans, may be obtained from both allogeneic and xenogeneic donors. Since islets from several donors are required to obtain normoglycemia and the lack of suitable human donors xenogeneic, preferably porcine, islets can be used. However, both allogeneic and xenogeneic islets elicit IBMIR when exposed to the blood of the recipient patient. As a consequence, within a few hours after transplantation the morphology of cells become disrupted and destroyed, generally manifested in loss of integrity, structure and form of the cells. This results in an initially greatly increased insulin release from the islets of Langerhans, followed by diminished or loss of insulin release. In other words, loss of normoglycemia soon follows the transplantation. Furthermore, IBMIR also causes graft-rejection of the cell transplants.

Administrations of conventional immunosuppressive drugs that prevent production of antibodies and organ-rejection have no effect on IBMIR or the graft-rejection of cell transplants caused by IBMIR. This indicates that the main mechanisms of IBMIR and graft-rejection of cell transplants differs from the rejection mechanism found in transplantation of whole organs and vascularized tissue.

Hereinafter follows a more detailed survey of the symptoms of IBMIR, and in particular platelet consumption, coagulation and complement activation and leukocyte infiltration. Furthermore, the effects of dextran sulfate on the respective symptoms are surveyed. For a more detailed discussion of these effects of dextran sulfate, reference is made to the example section.

Starting with platelet consumption, IBMIR affects the platelet count of blood exposed to allogeneic or xenogeneic cells or cell clusters. A significant decrease in free circulating platelets can be detected in the blood following the blood-cell contact. The platelets become activated and adhere to the cells, resulting in a platelet aggregation. Following adhesion to the cells, the platelets release several substances including platelet phospholipids, which are important for clot formation and activation of the coagulation system.

Administration of an effective amount of dextran sulfate according to the invention inhibits the consumption of platelets as seen as an increase in the platelet count of the blood, which returns to the value measured in the blood before exposure to foreign cells or cell clusters. In addition, platelet adhering to the cells is considerably diminished by dextran sulfate, although trace amounts of platelets surrounding the islets may still be observed. The effect of these remaining platelets is, however, not necessarily a disadvantage. Animal studies have shown that after transplantation, at least one week elapses before angiogenesis is detected [15, 16]. Platelets contain a number of important growth factors, such as platelet-derived growth factor (PDGF), vascular endothelial growth factor (VEGF), and fibroblast growth factor (FGF) [17, 18], which may support revascularization and islet engraftment in the body of the patient. In the case of clinical islet transplantation, when islets are embolized into the portal vein, a wreath of adhering platelets might, in a similar way, support their engraftment and survival in the liver tissue.

Upon contact with blood, the foreign cells activates the coagulation system, through the expression of tissue factors on the cells and through substances released by the adhering and aggregating platelets. Briefly, tissue factor (TF) produced by the cells complexes with blood coagulation factor VIIa and acts enzymatically on factor X to form activated factor X (FXa). Thereafter follows a cascade of activation of different factors, which eventually results in generation of thrombin from prothrombin. Thrombin in turn causes polymerization of fibrinogen molecules into fibrin fibers forming a fibrin clot around the cells, which is all well known to a person skilled in the art. Thrombin also activates the intrinsic pathway for initiating blood clotting, in which factor XII (Hageman factor) becomes activated (FXIIa) and in turn enzymatically activates factor XI (thrombobplastin antecedent), resulting in FXIa, the activated form of factor XI. Also this pathway eventually results in generation of thrombin from prothrombin as for the extrinsic TF-activated pathway.

The blood clotting may be inhibited by antithrombin, a circulating serine protease inhibitor, which inactivates FXIIa, FXIa and thrombin, forming factor XIIa-antithrombin (FXIIa-AT), factor XIa-antithrombin (FXIa-AT) and thrombin-antithrombin (TAT) complexes. In addition, C1 esterase inhibitor is a known inhibitor of FXIa and FXIIa forming factor XIa-C1 esterase inhibitor (FXIa-C1 INH) and factor XIIa-C1 esterase inhibitor (FXIIa-C1 INH) complexes.

A once formed fibrin clot around the cells or cell clusters may be removed by the action of plasmin of the fibrinolytic system. Plasmin degrades the fibrin clot into fibrin degradation products, thereby preventing further clotting. However, the action of plasmin is inhibited by alpha 2 antiplasmin, which binds to and inactivates free plasmin forming a plasmin-alpha 2 antiplasmin (PAP) complex.

IBMIR is characterized by formation of fibrin clots around cells exposed to foreign blood in vitro and in vivo. In addition, an increase in FXIa-AT, FXIIa-AT, TAT and PAP is detected. IBMIR has no effect on either the amount of FXIa-C1 INH or FXIIa-C1 INH. Administration of an effective amount of dextran sulfate according to the invention abrogates the effect of IBMIR on coagulation activation, which is manifested in a decrease in the amount of FXIa-AT, FXIIa-AT, TAT and PAP detected in the blood. The effect of dextran sulfate on the coagulation activation may be mediated through the coagulation system per se, through the inhibitory effect of dextran sulfate on the platelet activation or both.

Following platelet and coagulation activation, a complement cascade follows in IBMIR. One of the components of the complement system is C3, which when activated is cleaved into the small C3a fragment, a peptide mediator of inflammation, and the larger fragment C3b. C3b in turn binds to other components of the complement system forming C5 convertase, which cleaves C5 into C5a, which diffuses away, and the active form C5b, which attaches to the cell surface. The bound C5b then binds to four more complement components forming the membrane attack complex c5b-9. This complex displaces the membrane phospholipids forming large transmembrane channels, which disrupts the membrane and enables ions and small molecules to diffuse freely. Thus, the cell cannot maintain its osmotic stability and is lysed by an influx of water and loss of electrolytes.

Most of the platelet consumption has already occurred before the complement mediated effects of IBMIR can be detected, suggesting that the clotting reaction may induce complement activation. IBMIR causes significant complement activation as measured by an increase of C3a and soluble membrane attack complex sC5b-9 in the blood. Administration of an effective amount of dextran sulfate according to the invention reduces the amount of these complement components in a dose dependent manner in the blood.

IBMIR is also characterized by infiltration of leukocytes into the cells or cell clusters. Infiltration of CD11b$^+$ polymorphonuclear cells and monocytes into the cells is clearly detected by immunohistochemical staining. Immunohistochemical analyses showed that the leukocyte infiltration was totally abrogated by administration of dextran sulfate.

According to a first aspect of the invention there is provided use of dextran sulfate, or a pharmaceutically acceptable derivate thereof, in manufacturing of a medicament for the treatment of Instant Blood-Mediated Inflammatory Reaction (IBMIR).

According to another aspect of the invention there is provided use of dextran sulfate, or a pharmaceutically acceptable derivate thereof, in the manufacturing of a medicament for the treatment of morphological disruption of transplanted cell transplants. Also use of dextran sulfate, or a pharmaceutically acceptable derivate thereof, in the manufacturing of a medicament for the treatment of graft-rejection of cell transplants is within the scope of the present invention. These two effects, i.e. disruption of cell morphology and graft-rejection, on transplanted cells, cell clusters or non-vascularized tissue in a mammalian, preferably human, patient are due the deleterious effect of IBMIR. The IBMIR-mediated effect on cell transplantation occurs both in human-to-human transplantation with ABO-matched donors, and using other mammalian, preferably pig, donors. Thus, dextran sulfate has an advantageous therapeutic effect in both allogeneic and xenogeneic cell transplantation.

For avoidance of doubt, as used herein, the term "treatment" includes the therapeutic and/or prophylactic treatment IBMIR. "Pharmaceutically acceptable derivates" includes salts and solvates.

The dextran sulfate, or derivates thereof, employed according to the invention may have a molecular weight from low molecular weight dextran sulfate (LMW-DS), e.g. from a few hundred or thousand Dalton (Da), to high molecular weight dextran sulfate (HMW-DS), generally with a molecular weight over 500 000 Da, e.g. >1 000 000 Da. The advantageous effect of dextran sulfate is especially prominent for LMW-DS, but positive effect is also seen by administration of dextran sulfate with a higher molecular weight. However, larger dextran sulfate molecules may activate FXII resulting in some side-effects, which is discussed in more detail below. The advantageous effect of larger dextran sulfate molecules on IBMIR according to the invention may be enhanced by increasing the sulfur content, i.e. the number of sulfate groups per glucosyl residue in the dextran chain. LMW-DS generally has an average molecular weight of below 20 000 Da, such as below 10 000 Da and e.g. about 5 000 Da. The average sulfur content for LMW-DS may be about 10 to 25%, such as 15 to 20%, corresponding to about 2 sulfate groups per glucosyl residue. For dextran sulfate with an average molecular weight higher than 20 000 Da, a larger sulfur content could be employed.

According to yet another aspect of the invention there is provided a method of treatment of IBMIR which comprises administering a therapeutically effective amount of dextran sulfate, or a pharmaceutical acceptable derivate thereof, to a patient in need of such treatment.

Further aspects of the invention are a method of treatment of graft-rejection of cell transplants which comprises administering a therapeutically effective amount of dextran sulfate, or a pharmaceutical acceptable derivate thereof, to a patient in need of such treatment, and a method of treatment of morphological disruption of transplanted cell transplants which comprises administering a therapeutically effective amount of dextran sulfate, or a pharmaceutical acceptable derivate thereof, to a patient in need of such treatment.

Dextran sulfate, and derivates thereof, may be administered for systemic delivery to the site of IBMIR or cell transplantation, or may be administered for delivery directly (locally) to that site, using appropriate means of administration that are known to the skilled person.

Thus, in accordance with the invention, dextran sulfate, and derivates thereof, may be administered orally, intravenously, intraperitoneally, subcutaneously, buccally, rectally, dermally, nasally, tracheally, bronchially, topically, by any other patenteral route or via inhalation, in the form of a pharmaceutical preparation comprising the active ingredient in a pharmaceutically acceptable dosage form. Depending on the form of cell transplantation, the site of transplantation, and the patient, to be treated, as well as the route of administration, the compositions may be administered at varying doses.

In therapeutic treatment of mammals, and especially humans, dextran sulfate and derivates thereof, may be administered alone, but will generally be administered as a pharmaceutical formulation in admixture with a pharmaceutically acceptable adjuvant, diluent or carrier, which may be selected with due regard to the intended route of administration and standard pharmaceutical practice.

The amounts of dextran sulfate, or derivates thereof, in the formulation will depend on the severity of the condition, and on the patient to be treated, as well as the actual formulation and administration route employed, and may be determined non-inventively by the skilled person. The concentration of administered dextran sulfate, or derivates thereof, according to the present invention should not be too high in order to minimize any side-effects associated with dextran sulfate. In most clinical situations suitable doses of dextran sulfate, or derivates thereof, in the therapeutic and/or prophylactic treatment of mammalian, especially human, patients are those that give a mean blood concentration below 5 mg/ml, probably less than 2 mg/ml and especially less than 1 mg/ml. A preferred concentration range is between 0.01 mg/ml and 1 mg/ml dextran sulfate, such as more than 0.05 mg/ml, more than 0.08 mg/ml or more than 0.1 mg/ml and/or less than 0.8 mg/ml, less than 0.6 mg/ml, less than 0.4 mg/ml or less than 0.2 mg/ml, e.g. within the concentration range of 0.01 mg/ml and 0.2 mg/ml and/or 0.05 mg/ml and 0.2 mg/ml. These concentrations have proven large enough to prevent or inhibit IBMIR and morphological disruption and graft-rejection of cell transplants, but is still low enough to minimize any side-effects usually associated with administration of dextran sulfate. In addition, culturing islets in LMW-DS did not have any adverse effect on islet function at concentrations ranging from 0.01 to 1 mg/ml. In any event, the physician or the skilled person will be able to determine the actual dosage, which will be most suitable for an individual patient, which may vary with the age, weight and response of the particular patient. The above-identified dosages are examples of preferred dosages of the average case. However, there can be individual instances where higher or lower dosage ranges are merited, and such are within the scope of the invention.

Today, dextran sulfate has already been used in clinical studies for anti-viral therapy against HIV, treatment of acute cerebral infarction in combination with urokinase, and in anti-hyperlipidemic therapy, in which dextran sulfate is coupled to a solid phase. In the two former types of studies the injection rate was about 45 mg/hour, which was maintained for a period of 2-3 weeks by continuous injection of dextran sulfate (MW 8 000 Da) and the blood concentration was found to be approximately 0.01 mg/ml. In all these patients thrombocytopenia (sometimes associated with bleeding) was observed after 3 days treatment, and alopecia was reported in about half of the patients. However, both these effects were reversible. It is estimated that administration of dextran sulfate for inhibiting IBMIR, morphological disruption and/or graft-rejection of cell transplants is usually performed for up to 1-2, or a few days. Therefore, the side-effects identified above will be very gentle during such a short administration period (a few days as compared to 2-3 weeks).

It has long been known that dextran sulfate induces hypotension via the release of bradykinin resulting from the activation of plasma kallikrein. However, this observation has primarily been made when HMW-DS has been immobilized in plasmapheresis columns for the treatment of hyperlipidemia and not during injection of dextran sulfate. This effect is a consequence of the direct activation of FXII to FXIIa. However, in the present document support is given that the factor XII is not directly activated by LMW-DS. As has been mentioned in the foregoing, the FXIIa-AT and PAP levels are elevated when cells are exposed to foreign blood without LMW-DS. However, these high levels are normalized when LMW-DS is added.

In order to prevent IBMIR following cell transplantation, and/or morphological disruption and graft-rejection of the cell transplants, a therapeutic concentration of dextran sulfate, or derivates thereof, is preferably attained, at least locally, at the site of transplantation, once the cell transplantation is performed. This may be obtained by administrating the dextran sulfate prior the actual transplantation. Alternatively, the cells or cell clusters to be transplanted into a patient may be injected dissolved in a solution comprising the dextran sulfate according to the present invention. The concentration of dextran sulfate in such a cell and dextran sulfate solution is preferably high enough, so that a therapeutic concentration of dextran sulfate, i.e. preferably less than 5 mg/ml, and more preferably within 0.01 mg/ml to 1.0 mg/ml, can be (locally) obtained in the site of transplantation for the first hours following transplantation. As a person skilled in the art understands the actual concentration of dextran sulfate, or derivates thereof, may temporarily be higher than the optimal concentration in the blood of the patient when cells or cell clusters are transplanted dissolved in a solution with dextran sulfate. Subsequently, the dextran sulfate will diffuse from the site of transplantation lowering the local dextran sulfate concentration. In some applications, no extra dextran sulfate is required to inhibit IBMIR, morphological disruption and/or graft-rejection of the cell transplants, since a therapeutic concentration of dextran sulfate may probably only be required up to the first 24-48 hours after transplantation. However, whenever required, additional dextran sulfate may be added, e.g. intravenously, intraperitoneally, or by some other administration route identified above. As a person skilled in the art understands, administration of a dextran sulfate solution comprising the cells or cell clusters to be transplanted may also be combined with administration of dextran sulfate, or derivates thereof, prior to the actual transplantation.

According to a further aspect of the invention there is provided a pharmaceutical formulation for use in the treatment of IBMIR comprising an effective amount of dextran sulfate, or a pharmaceutical acceptable derivate thereof.

The present invention is also directed to a pharmaceutical formulation for use in the treatment of graft-rejection of cell transplants comprising an effective amount of dextran sulfate, or a pharmaceutical acceptable derivate thereof, and a pharmaceutical formulation for use in the treatment of morphological disruption of transplanted cell transplants comprising an effective amount of dextran sulfate, or a pharmaceutical acceptable derivate thereof.

Dextran sulfate, and derivates thereof, may also be combined with other therapeutic agents that are useful in the treatment of graft-rejection of transplanted tissue. Suitable, but not limiting examples of such immunosuppressive agents that may be used together with dextran sulfate for treatment of graft-rejection are cyclosporin, tacrolimus, corticosteroids, rapamycin (sirolimus) and mycophenolate mofetil. Administration of dextran sulfate, or derivates thereof, according to the invention may also be coordinated with administration of anti-TF antibodies and/or site-inactivated factor VIIa, which have been shown to have some functionality in inhibiting IBMIR.

EXAMPLES

Reagents

Low molecular weight dextran sulfate (LMW-DS) with an average molecular weight of 5 000 Da and a sulfur content of approximately 17% was obtained from Sigma Chemicals (St. Louis, Mo., USA). High molecular weight dextran sulfate (HMW-DS) having an average molecular weight of >1 000 000 Da and sulfur content of 16-19% was purchased from Amersham Bioscience (Uppsala, Sweden). Low molecular weight dextran (LMW-D; MW 5 000 Da) and high molecular weight dextran (HMW-D; MW>1 000 000 Da) were obtained from Fluka Chemical (Buchs, Switzerland) and Sigma Chemicals (St. Louis, Mo., USA), respectively.

Heparin Treatment

All materials that were in contact with whole blood were furnished with a Corline heparin surface (Corline Systems AB, Uppsala, Sweden) according to the manufacturer's recommendation. The surface concentration of heparin was 0.5 $\mu g/cm^2$, corresponding to approximately 0.1 $U/cm^2$, with an antithrombin binding capacity of 2-4 $pmol/cm^2$.

Preparation of Blood

Fresh human blood, obtained from healthy volunteers who had received no medication for at least 14 days, was collected in surface-heparinized 60-ml syringes (18 gauge, Microlance; Becton Dickinson, Franklin Lakes, N.J.). The cannulae of the syringes were connected to surface-heparinized silicon tubing. During sampling, the syringes were rotated continuously.

Animals

Male inbred athymic mice (nu/nu Black-6, BomMice) from Bomholt Gaard Breeding and Research Centre, Ltd. (Ry, Denmark), 20-25 g, were used as recipients. All animals had free access to a standard diet and water.

Islet Isolation

Adult porcine islets (API) were isolated from the pancreata of 2- to 3-year-old Swedish Landrace sows (200 to 300 kg) by means of an enzymatic and mechanical pancreatic digestion procedure followed by filtration and separation of the islets on Ficoll gradients as suggested by Ricordi et al. [19, 20]. The islets were suspended in M199 culture medium (GIBCO, BRL, Life Technologies LTD., Paisley, Scotland) supplemented with 10% porcine serum (GIBCO, BRL), 1 mM calcium nitrate, 0.02 µM selenium, 20 mM nicotinamide, 25 mM HEPES, Fungizone (500 µg/l), and gentamicin (50 mg/l) and cultured in 250-ml flasks at 37° C. in 5% $CO_2$ and humidified air for 1 to 4 days. The culture medium was changed on day 1 and then every other day thereafter. Islet volume and purity were determined under an inverted microscope after staining with a dithizone (Sigma Chemicals, St. Louis, Mo.).

Induction of Diabetes in Athymic Mice

Diabetes was induced in athymic mice by intravenous (i.v.) injection of steptozotocin from Sigma Chemicals (Palo Alto, Calif., USA) according to Wennberg et al. [20]. The steptozotocin dose was 250 mg/kg body weight for the athymic mice. An animal was considered diabetic if its blood glucose (B-glucose) level exceeded 20 mmol/l (>360 mg/dl) for 2 or more consecutive days.

Transplantation of API into Diabetic Athymic Mice Treated with or without LMW-DS After being cultured for 4 days, 5 µl of API (5000 IEQs) from five isolations were transplanted into the liver via the portal vein of 11 male inbred diabetic athymic mice, which were anesthetized during surgery with isoflurene. Five mice were treated i.v. with LMW-DS. 0.15 mg of LMW-DS was injected 10 minutes before transplantation, and an additional 0.3 mg was injected 6 hours after transplantation. Thereafter, LMW-DS was administered twice a day at 1-2, 3-4 and 5-6 days after transplantation in declining doses of 1, 0.5 and 0.25 mg, respectively. Six (untreated) mice were injected with an equivalent volume of saline in the same manner.

Statistical Analysis

All values were expressed as mean±SEM and compared using Friedman ANOVA (Table 1), Student's paired t-test (Table 3), the Wilcoxon signed rank test (Table 4), and one-way factorial ANOVA following Scheffe's post hoc test (Table 5). In the morphological study of transplanted islets, the frequency of clot formation and the intensity of leukocyte infiltration were evaluated using the Wilcoxon rank sum test. P-values<0.05 were considered statistically significant.

Islet Quality

A static glucose stimulation (SGS) test was performed as a functional test for API. Fifteen islets were hand-picked and gently shaken in Krebs-Ringer bicarbonate containing 1.6 mM glucose at 37° C. for 60 min. Thereafter, the glucose concentration was switched to 16.7 mM for an additional 60 min. Supernatants were collected and stored at −20° C. until analysis. The insulin content in the supernatants was analyzed by ELISA (DAKO Diagnostics, Ltd., Ely, UK). The stimulator index was calculated as a ratio of the insulin concentration at high glucose and low glucose, respectively. The purity of the API used in this study ranged from 81 to 95% (mean, 88.5±2.2%). The stimulation index in the static glucose stimulation test was between 0.8 and 7.8 (3.4±1.2), and the mean insulin content was 85.5±6.2 pmol/µg DNA.

In addition, the ADP/ATP ratio was measured to evaluate the viability of cultured API, using the ApoGlow™ kit (LumiTech, Ltd., Nottingham, UK). In brief, 75 islet equivalents (IEQ) of API were washed in PBS and then mixed with 100 µl of nucleotide-releasing reagent for 10 min at room temperature. Thereafter, 20 µl of nucleotide-monitoring reagent was added to the solution, and the ATP levels were measured using a luminometer (FB 12 Luminometer, Berthold Detection Systems GmbH, Pforzheim, Germany) and expressed as the number of relative light units (RLU). After 10 min, the ADP in the solution was converted to ATP by the addition of 20 µl of ADP-converting reagent and then measured as the number of RLU. Subsequently, the ADP/ATP ratio in the API was calculated as suggested by Bradbury et al. [21]. The insulin/DNA ratio in the API was measured according to Wennberg et al. [22] and expressed as pmol/µg. The survival ratio of cultured API was calculated as a percentage of IEQ values obtained on day 3 compared to day 0.

Any possible toxicity of LMW-DS was assessed by culturing API from three different pancreata in the presence (0.01, 0.1, or 1 mg/ml) or absence of LMW-DS for 3 days. The results of the survival rate, stimulation index, ADP/ATP ratio and insulin/DNA ratio for control samples and for samples with the three different LMW-DS concentrations are presented in Table 1 below. LMW-DS showed no adverse effect on the function, viability, or survival rate of API at any of the concentrations tested. Furthermore, there was no difference between the morphology of the LMW-DS-treated API and that of API cultured in the absence of LMW-DS.

TABLE 1

|  | API cultured without LMW-DS | API cultured with LMW-DS (0.01 mg/ml) | API cultured with LMW-DS (0.1 mg/ml) | API cultured with LMW-DS (1 mg/ml) |
| --- | --- | --- | --- | --- |
| Survival rate (% IEQ) | 57.0 ± 5.2 | 43.6 ± 6.7 | 58.4 ± 4.3 | 68.9 ± 2.6 |
| Stimulation Index in SGS test | 1.77 ± 0.17 | 2.26 ± 0.51 | 3.22 ± 0.89 | 1.42 ± 0.35 |
| ADP/ATP ratio | 0.11 ± 0.03 | 0.08 ± 0.03 | 0.10 ± 0.03 | 0.11 ± 0.01 |
| Insulin/DNA ratio (pmol/μg) | 79.0 ± 11.4 | 66.1 ± 5.8 | 69.1 ± 9.6 | 71.6 ± 7.4 |

Clotting Time

Blood was drawn from four healthy volunteers into Vacutainer™ tubes containing citrate. Whole blood (980 μl) was incubated with 2 μl of API at 37° C. in polypropylene sample cups in a ReoRox™ rheometer (Global Haemostasis International, Gothenburg, Sweden). The coagulation reaction was started by adding 20 μl of 1M $CaCl_2$ in the presence or absence of different kinds of dextran (LMW-DS, HMW-DS, LMW-D and HMW-D). Every 6 s, the cup was set into free torsional oscillation around its vertical axis, and the damping and frequency of the oscillation was registered. Clotting time was identified as the point of maximal damping.

The results obtained from the clotting time experiments are presented in Table 2 below. API incubated in citrated human blood induced clot formation promptly, at an average of 6.1±0.3 min after calcification. Clot formation was totally abrogated in the presence of LMW-DS at all doses tested, whereas HMW-DS inhibited clot formation only at 0.1 mg/ml. Both LMW-D and HMW-D extended the clotting time to only a minor degree compared to control samples (no additives). Thus, sulfation of DS seems to be crucial for the inhibitory capacity observed.

TABLE 2

|  | experiment 1 | experiment 2 | experiment 3 | experiment 4 |
| --- | --- | --- | --- | --- |
| No additives | 5.6 | 6.3 | 6.9 | 5.5 |
| LMW-DS (0.01 mg/ml) | >60 | >60 | >60 | >60 |
| LMW-DS (0.1 mg/ml) | >60 | >60 | >60 | >60 |
| HMW-DS (0.01 mg/ml) | 15.8 | 36.9 | 21.0 | 38.3 |
| HMW-DS (0.1 mg/ml) | >60 | >60 | >60 | >60 |
| LMW-D (0.01 mg/ml) | 19.2 | 11.3 | | |
| LMW-D (0.1 mg/ml) | 25.2 | 25.8 | | |
| HMW-D (0.01 mg/ml) | 19.8 | 13.8 | | |
| HMW-D (0.1 mg/ml) | 14.2 | 33.2 | | |

Inhibition of IBMIR by LMW-DS

Adult porcine islet perfusion in heparinized PVC tubing loops was used as a model for assaying the effect of LMW-DS on IBMIR and pig-to-human xenotransplantation. This protocol is basically performed as previously described [4, 23] with some modifications. In general words, loops made of PVC (diameter 6.3 mm, length 390 mm), whose inner surface was furnished with immobilized heparin, were used. The tubing was held together with a specially designed heparinized connector. A circular loop was formed when the ends of the connector were tightly pushed into the lumen of the tubing ends. A rocking apparatus, placed in a 37° C. incubator, was used to generate blood flow inside the loops. The loops were rocked at a setting that prevented the blood from coming in contact with the connectors.

Seven 60-min islet experiments were performed, using API isolated from four different pigs. LMW-DS, dissolved in saline, was tested at 0, 0.01, 0.1, and 1 mg/ml (final concentration). For each experiment, one loop containing fresh human blood and saline without API was included as a control. In two experiments, one loop containing fresh human blood and 1 mg/ml of LMW-DS without API was included. Concurrently, pre-incubation of human blood with 1 mg/ml of LMW-dextran, which was not sulfated, was tested in five experiments. In each experiment, 7 ml of fresh human blood from the same donor was added to each loop. The loops were then placed on the rocking device for 5 min with either LMW-DS or saline. Thereafter, the loops were opened, and 100 μl of saline with or without 5 μl of API (approximately 5,000 IEQ) was added to the loops and followed by another 60-min incubation on the rocking device at 37° C. Blood glucose levels were measured with a glucometer (Glucometer Elite; Bayer Diagnostics, Leverkusen, Germany) before the perfusion.

After every perfusion, the loop contents were filtered through 70 μm-diameter filters (Filcons, Cuptype; DAKO, Denmark). Both macroscopic blood clots and tissue recovered on the filters were snap-frozen in isopentane for immunohistochemical staining. The remaining filtered blood was collected in 4.1 mM EDTA (final concentration) and used for hematological analysis (platelets, lymphocytes, monocytes, and granulocytes) and assays of coagulation activation (thrombin-antithrombin [TAT], factor XIa-antithrombin complexes [FXIa-AT], and factor XIIa-antithrombin complexes [FXIIa-AT]), fibrinolysis activation (plasmin-alpha 2 antiplasmin complexes [PAP]), complement activation (C3a and sC5b-9), and C1 esterase inhibitor activation (factor XIa-C1 esterase inhibitor [FXIa-C1 INH], factor XIIa-C1 esterase inhibitor [FXIIa-C1 INH]). Samples taken at 0, 15, and 30 min were also analyzed. In 0-min samples, the blood was not added to the tubing loop but was instead transferred immediately to the EDTA-containing tubes. The blood samples were centrifuged at 4° C. at 3290×g for 20 min, and the plasma was collected and stored at −70° C. until analyzed. Blood glucose levels before API perfusion ranged from 4.8 to 6.2 mmol/l.

Platelet counts and differential leukocyte counts were analyzed on a Coulter ACT-diff analyzer (Beckman Coulter, Fla., USA) using EDTA-treated blood. TAT and PAP were quantified using commercially available enzyme immunoassays (EIA) kits (Enzygnost TAT, Behringswerke, Marburg, Germany; Imuclone® PAP, American Diagnostica Inc., Greenwich, USA). FXIa-AT, FXIIa-AT, FXIa-C1 INH, and FXIIa-C1 INH were analyzed according to the method of Sanchez et al. [24]. C3a was analyzed as previously described by Nilsson Ekdahl et al. [25], and sC5b-9 was analyzed using a modification of the EIA described by Mollnes et al. [25, 26].

In tubing loops containing fresh human blood without API, blood cell counts and coagulation and complement parameters altered only slightly, as can be seen in Table 3 below. All these alterations are considered to be normal background changes resulting from interaction of the blood with the tubing surface and the fluid-air interface.

LMW-DS prevented macroscopic clotting, inhibited blood cell consumption, and reduced both coagulation and complement activation in a dose-dependent fashion (see Table 3). A significant increase in platelets in the LMW-DS treated blood could be seen at a concentration of 0.01 mg/ml of LMW-DS, demonstrating an restoration of blood cell counts to nearly normal levels already at this low concentration of LMW-DS. The coagulation activation products TAT, FXIa-AT and FXIIa-AT were suppressed at 0.01 mg/ml of LMW-DS, but FXIa-AT slightly increased again at doses ranging from 0.1 to 1 mg/ml LMW-DS.

Figure 2:
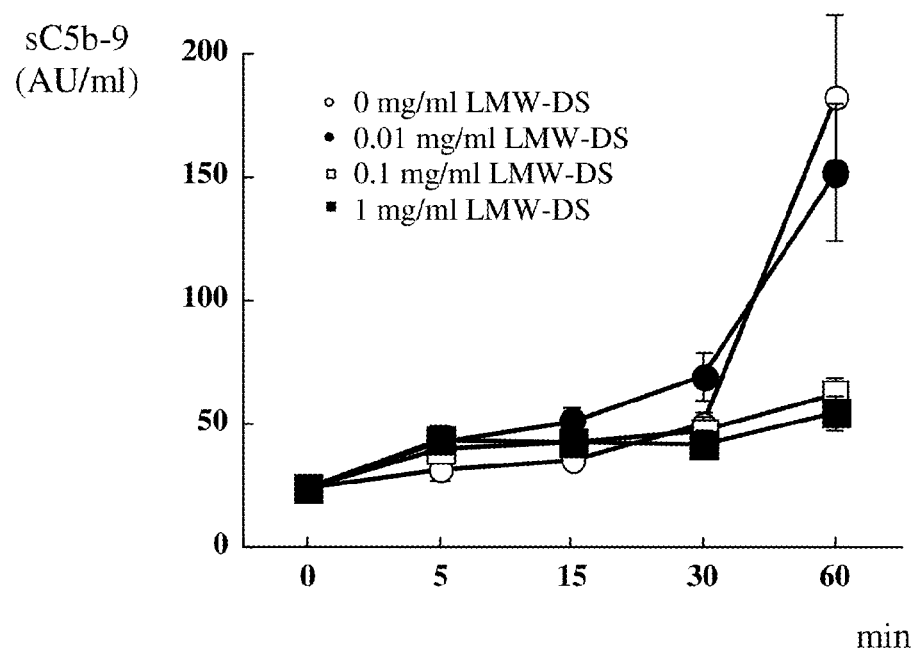
FIG. 2 is a diagram illustrating the effect of LMW-DS on the generation of sC5b-9 during perfusion of porcine islets with human blood.

LMW-DS reduces complement activation as assayed by generation of C3a and soluble membrane attack complex sC5b-9, as is seen in Table 3. FIG. 1 illustrates, in more detail, the effect of LMW-DS on the generation of C3a during 60 min of API perfusion with fresh human blood in the tubing loop model. In samples where LMW-DS was added, the dextran sulfate was pre-incubated with fresh human blood for 5 min prior to API perfusion with the blood. White circles corresponds to 0 mg/ml of LMW-DS, black circles represents 0.01 mg/ml LMW-DS and white squares and black squares corresponds to 0.1 mg/ml and 1 mg/ml of LMW-DS, respectively. A corresponding diagram of the effect of LMW-DS on the generation of sC5b-9 is found in FIG. 2. As is clearly seen from the diagrams of FIGS. 1 and 2, the main complement activation occurred about 30 min after API perfusion. Administration of 0.1 mg/ml and 1 mg/ml of LMW-DS totally inhibits generation of both C3a and the membrane attack complex sC5b-9, whereas the lower concentration of LMW-DS (0.01 mg/ml) significantly reduces generation of C3a.

FXIa-C1 INH was generated in none of the tubing loops tested during 60 min of perfusion (data not shown). FXIIa-C1 INH did not change either in the presence or in the absence of LMW-DS.

PAP was increased in the absence of LMW-DS, while significantly suppressed at 0.01 mg/ml of LMW-DS.

TABLE 4-continued

|  | LMW-DS (1 mg/ml, n = 5) | LMW-D (1 mg/ml, n = 5) |
|---|---|---|
| FXIa-AT (µmol/l) | 1.56 ± 0.82 | 1.09 ± 0.08 |
| C3a (ng/ml) | 171.5 ± 72.4* | 1490.3 ± 406.4 |
| sC5b-9 (AU/ml) | 41.6 ± 11.5* | 157.3 ± 19.1 |

*Significant difference compared to the API loops with LMW-D by use of Wilcoxon signed rank test.

Direct Effect of LMW-DS on the Complement System in Human Serum

The direct effect of LMW-DS on the complement cascade was investigated by incubating human serum in the polypropylene tube. Serum (1 ml) was added to each tube together with LMW-DS at a final concentration of 0, 0.01, 0.1, or 1 mg/ml. At 5, 10, 15, 30, 45, and 60 min after serum incubation at 37° C., 100 µl of serum was transferred to tubes containing 10 mM EDTA. These samples were stored at −70° C. before analysis of the complement components C3a and sC5b-9.

TABLE 3

|  | Before perfusion (n = 7) | After perfusion | | | | |
|---|---|---|---|---|---|---|
|  |  | No API (n = 7) | API with LMW-DS (mg/ml) | | | |
|  |  |  | 0 (n = 7) | 0.01 (n = 7) | 0.1 (n = 7) | 1 (n = 7) |
| Platelets (×10⁹/l) | 252.7 ± 9.9 | 141.8 ± 11.8 | 6.4 ± 5.6 | 108.2 ± 12.9* | 146.1 ± 8.1* | 162.3 ± 8.9* |
| Lymphocytes (×10⁹/l) | 2.15 ± 0.09 | 2.04 ± 0.10 | 1.66 ± 0.21 | 1.90 ± 0.11 | 1.91 ± 0.12 | 1.89 ± 0.10 |
| Monocytes (×10⁹/l) | 0.39 ± 0.06 | 0.31 ± 0.02 | 0.15 ± 0.03 | 0.48 ± 0.10 | 0.40 ± 0.07* | 0.31 ± 0.05* |
| Granulocytes (×10⁹/l) | 2.90 ± 0.35 | 2.66 ± 0.36 | 1.17 ± 0.34 | 2.20 ± 0.40 | 2.80 ± 0.50* | 2.92 ± 0.37* |
| TAT (µg/ml) | 9.0 ± 3.7 | 144.0 ± 63.8 | 7042.5 ± 1314.1 | 645.3 ± 177.4* | 61.0 ± 8.6* | 15.0 ± 5.6* |
| FXIa-AT (µmol/l) | 0.03 ± 0.01 | 0.10 ± 0.03 | 3.00 ± 0.60 | 0.13 ± 0.01* | 0.08 ± 0.01 | 1.17 ± 0.41* |
| FXIIa-AT (µmol/l) | 0.05 ± 0.01 | 0.06 ± 0.01 | 2.02 ± 0.63 | 0.08 ± 0.02* |  |  |
| C3a (ng/ml) | 63.0 ± 7.8 | 590.2 ± 105.3 | 1122.5 ± 132.0 | 630.6 ± 103.4* | 191.7 ± 36.6* | 215.6 ± 52.2* |
| sC5b-9 (AU/ml) | 24.0 ± 2.7 | 104.7 ± 20.7 | 182.1 ± 33.4 | 151.4 ± 27.9 | 61.9 ± 6.5* | 53.9 ± 7.1* |
| FXIIa-C1 inh (µmol/ml) | 0.07 ± 0.01 | 0.09 ± 0.03 | 0.06 ± 0.01 | 0.10 ± 0.03 |  |  |
| PAP (ng/ml) | 585.7 ± 240.9 | 443.6 ± 179.4 | 1012.5 ± 224.0 | 398.2 ± 60.7* |  |  |

*Significant difference compared to the API loops without LMW-DS by use of Student's t test.

The effect of LMW-dextran on blood cell counts, coagulation and complement parameters after 60 min of API perfusion with fresh human blood was investigated by means of the tubing loop model similar to LMW-DS, as discussed above. A comparison between LMW-D and LMW-DS on the symptoms of IBMIR is found in table 4. LMW-dextran, which is not sulfated, had only a marginal effect on IBMIR. These data indicate that sulfation seems crucial for dextran's inhibitory effect on IBMIR triggered by API.

TABLE 4

|  | LMW-DS (1 mg/ml, n = 5) | LMW-D (1 mg/ml, n = 5) |
|---|---|---|
| Platelets (×10⁹/l) | 181.1 ± 16.3* | 44.9 ± 18.7 |
| Lymphocytes (×10⁹/l) | 1.94 ± 0.12 | 2.14 ± 0.32 |
| Monocytes (×10⁹/l) | 0.38 ± 0.10 | 0.29 ± 0.08 |
| Granulocytes (×10⁹/l) | 3.23 ± 0.21* | 1.90 ± 0.43 |
| TAT (µg/ml) | 12.8 ± 4.9* | 4429.2 ± 2002.5 |

Figure 3:
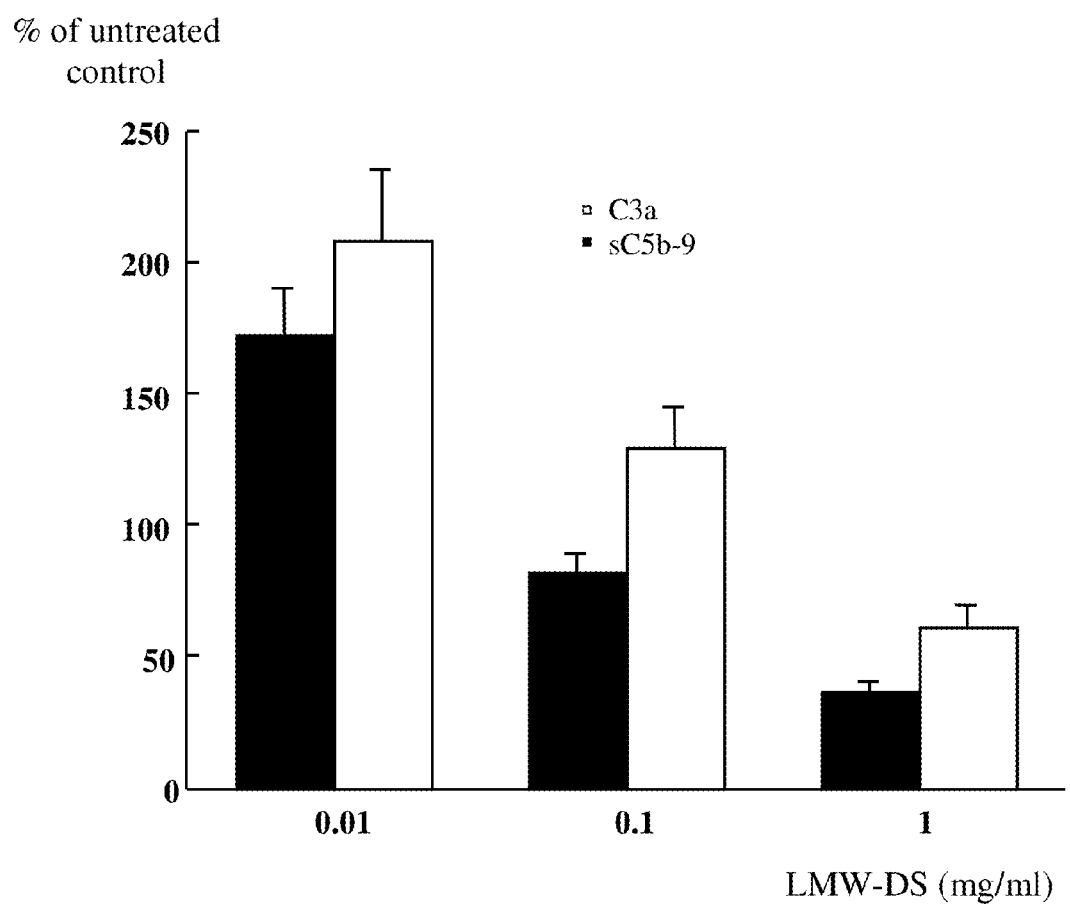
FIG. 3 is a diagram illustrating the direct effect of LMW-DS on the complement system when human serum is incubated in the presence of LMW-DS.

FIG. 3 illustrates the effect of LMW-DS on the presence of C3a and sC5b-9 of the complement system in human serum. The values are expressed as percentage of the amount of C3a and sC5b-9 in control samples (without LMW-DS). Filled bars represent generation of C3a and unfilled correspond to sC5b-9. At 0.01 mg/ml LMW-DS, an increased complement activation was reflected in an increased generation of both C3a and sC5b-9, but at 1 mg/ml an inhibitory effect was seen. Although the effects on whole blood and serum cannot be directly compared, LMW-DS by itself probably induces complement activation at the lowest doses of LMW-DS applied. At a higher concentration the inhibitory effect prevails.

Graft Survival in Diabetic Athymic Mice

Blood glucose levels were measured in blood obtained from tails of recipients using a Glucometer Elite® B-glucose measuring instrument (Bayer AB, Gothenburg, Sweden). Measurements were taken daily before 12 am and expressed as mmol/l (1 mmol/l≈18 mg/dl). Loss of graft function was considered to have occurred if B-glucose levels exceeded 11.1 mmol/l (>200 mg/dl) for 2 or more consecutive days. Post-transplant duration of normoglycemia (<200 mg/dl) was defined as the graft survival period.

All streptozotocin induced diabetic athymic mice were severely hyperglycemic before transplantation, with no differences of B-glucose levels seen among the various groups of recipients. The nonfasting B-glucose levels were reduced immediately after transplantation in all diabetic recipients implanted intraportally with API. However, untreated mice remained normoglycemic for only a limited time, see Table 5. B-glucose levels increased again during the first 3 days after transplantation in four of the six untreated mice. In contrast, normoglycemia was sustained for a significantly longer period in mice treated with LMW-DS than in untreated mice (8.8±1.9 days vs. 3.5±1.2 days, p=0.045, Table 5). All API used in the present study were shown to cure diabetic athymic mice when equivalent amounts were transplanted under the renal subcapsular space (removal of the graft-bearing kidney resulted promptly in an elevated blood glucose level).

TABLE 5

| Implantation site | Treatment | n | Individual graft survival (days) | Mean graft survival (days) |
|---|---|---|---|---|
| Liver | Saline | 6 | 1, 1, 2, 3, 6, 8 | 3.5 ± 1.2* |
|  | LMW-DS | 5 | 4, 6, 8, 12, 14 | 8.8 ± 1.9* |
| Kidney subcapsule | — | 5 | >56 (×5) | >56* |

*Significant among all groups.

Immunohistochemical Experiments

Islets and macroscopic clots were recovered on filters after 60 min of perfusion with blood and with LMW-DS (0.1 mg/ml and 1 mg/ml) or without LMW-DS (control), then collected in embedding medium (Tissue-Tek; Miles, Eckhart, Ind., USA) and snap-frozen in isopentane. Islets were sectioned and subsequently stained with horseradish peroxidase (HRP) conjugated mouse anti-human CD41a (R&D Systems, Abigdon, UK) and anti-CD11b$^+$ (Clone 2LPM 19c, DAKO, Carpinteria, Calif., USA). In the in vivo study, the API-containing mouse livers were retrieved 10 days after transplantation and snap-frozen in isopentane. The samples were sectioned and stained with guinea pig anti-insulin (DAKA, Carpinteria, Calif., USA) and rat anti-mouse CD11b$^+$ (Serotec Ltd. Scandinavia, Oslo, Norway).

Figure 4:
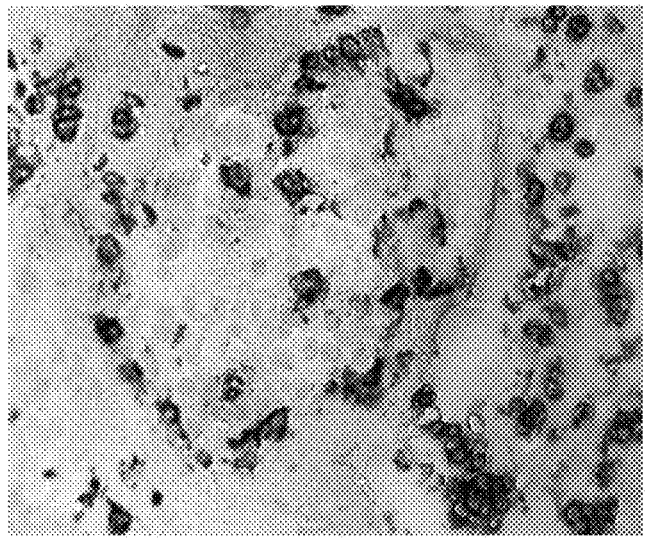
FIG. 4 illustrates distribution of leukocytes in porcine islets after perfusion with human blood containing no LMW-DS.
Figure 5:
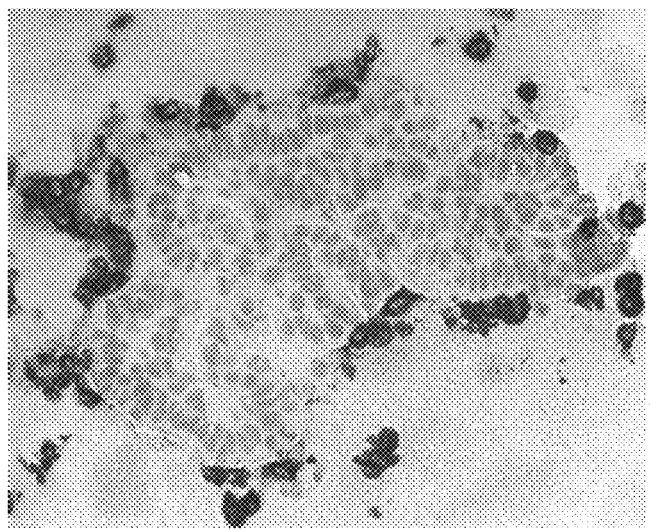
FIG. 5 illustrates distribution of leukocytes in porcine islets after perfusion with human blood containing 1 mg/ml LMW-DS.
Figure 6:
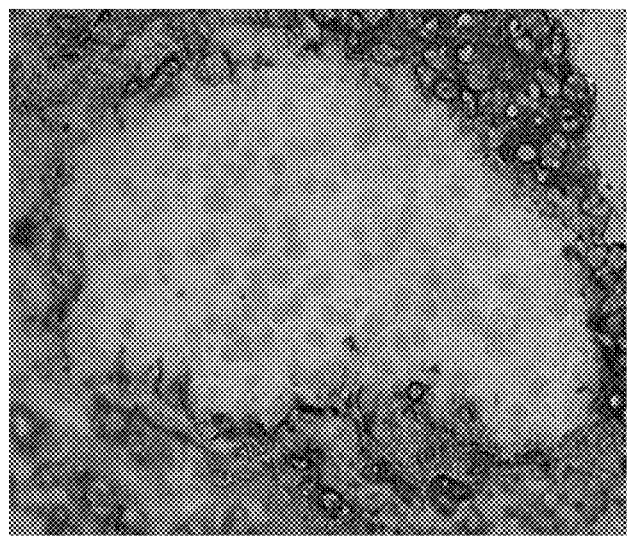
FIG. 6 illustrates distribution of platelets in porcine islets after perfusion with human blood containing no LMW-DS.
Figure 7:
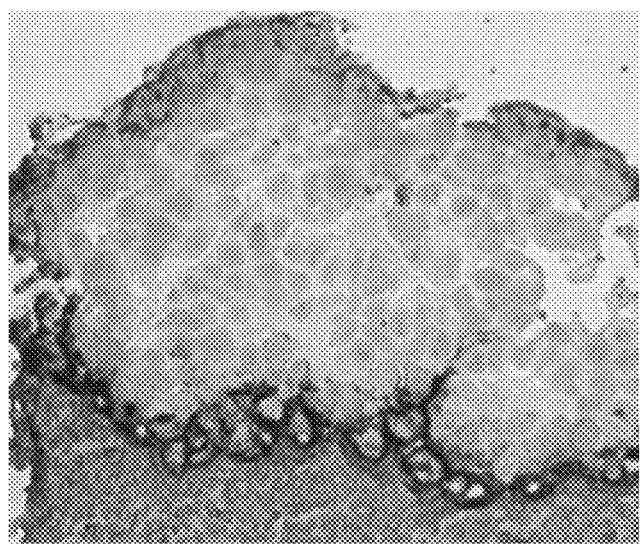
FIG. 7 illustrates distribution of platelets in porcine islets after perfusion with human blood containing 1 mg/ml LMW-DS.

After 60 min, islets retrieved from untreated control loops were consistently found to be embedded in clots. Immunohistochemical staining showed a capsule of fibrin and platelets surrounding the islets. FIG. 4 illustrates infiltration of CD11b$^+$ polymorphonuclear cells and monocytes into the control islets. In contrast, a complete inhibition of clot formation was seen, and the number of infiltrating CD11b$^+$ cells decreased considerably when 1 mg/ml of LMW-DS was added during the incubation, which is illustrated in FIG. 5. A similar effect was also observed at 0.1 mg/ml. The control samples also presented a thick layer of platelets adhering to the cells, as is seen in FIG. 6. A much thinner layer of platelets adhering to the islets was observed in the LMW-DS treated samples, illustrated in FIG. 7. Control islets not exposed to blood were negative in all staining used.

Figure 8:
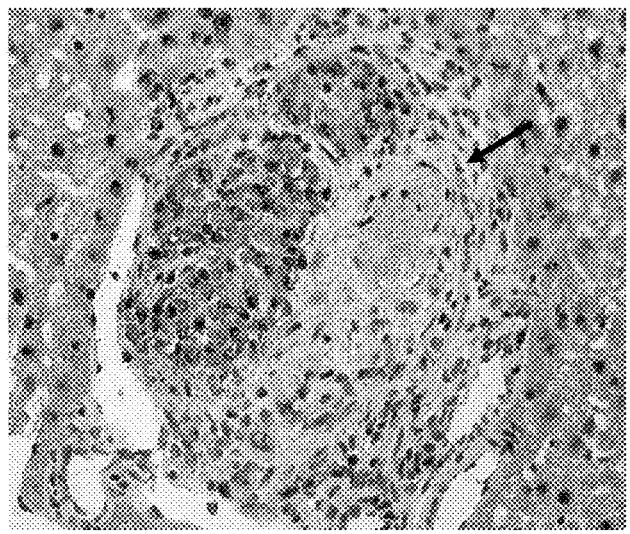
FIG. 8 illustrates expression of insulin in porcine islets after intraportal transplantation into diabetic athymic mice with no LMW-DS treatment.
Figure 9:
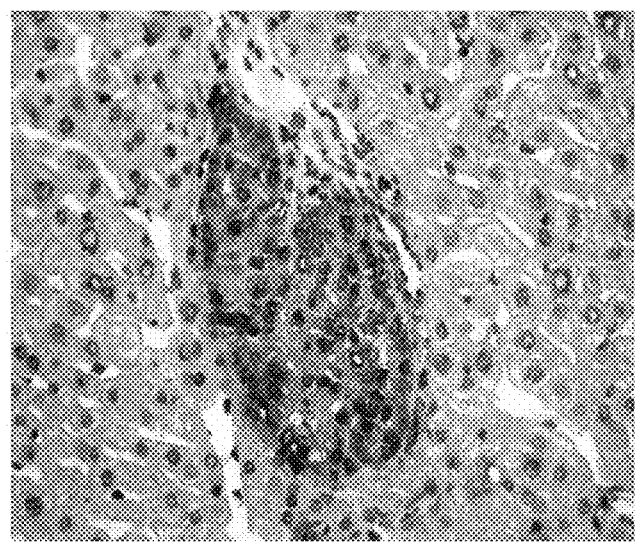
FIG. 9 illustrates expression of insulin in porcine islets after intraportal transplantation into diabetic athymic mice with LMW-DS treatment.
Figure 10:
FIG. 10 illustrates distribution of leukocytes in porcine islets after intraportal transplantation into diabetic athymic mice with no LMW-DS treatment.
Figure 11:
FIG. 11 illustrates distribution of leukocytes in porcine islets after intraportal transplantation into diabetic athymic mice with LMW-DS treatment.

Most of the islets retrieved from untreated mice were entrapped in clots, as is illustrated in FIG. 8. In this FIG. 8, the arrow represents thrombus formation with entrapped porcine islets. However, only a few islets from LMW-DS treated mice were entrapped, which is illustrated in FIG. 9. Immunohistochemical staining showed an infiltration of CD11b$^+$ (MAC-1$^+$) leukocytes into the islets retrieved from untreated mice, as is seen in FIG. 10. In contrast, there were markedly fewer infiltrating CD11b$^+$ (MAC-1$^+$) cells in LMW-DS treated mice, illustrated in FIG. 11. The frequency of clot formation and intensity of leukocyte infiltration were significantly lower in LMW-DS treated recipients than in untreated recipients (p=0.034). FIGS. 4 to 9 are at 200× magnification and FIGS. 10 and 11 at 100× magnification.

It will be understood a person skilled in the art that various modifications and changes may be made to the present invention without departure from the scope thereof, which is defined by the appended claims.

REFERENCES

[1] Shapiro A M, et al., "Islet transplantation in seven patients with type 1 diabetes mellitus using a glucocorticoid-free immunosuppressive regimen", *N Engl J Med*, Vol. 343, No. 4, pp. 230-238 (2000)

[2] Ryan E A, et al., "Clinical outcomes and insulin secretion after islet transplantation with the Edmonton protocol", *Diabetes*, Vol. 50, No. 4, pp. 710-719 (2001)

[3] Bennet W, et al., "Damage to porcine islets of Langerhans after exposure to human blood in vitro, or after intraportal transplantation to cynomologus monkeys: protective effects of sCR1 and heparin", *Transplantation*, Vol. 69, No. 5, pp. 711-719 (2000)

[4] Bennet W, et al., "Incompatibility between human blood and isolated islets of Langerhans: a finding with implications for clinical intraportal islet transplantation?", *Diabetes*, Vol. 48, No. 10, pp. 1907-1914 (1999)

[5] Buhler L, et al., "Adult porcine islet transplantation in baboons treated with conventional immunosuppression or a non-myeloablative regimen and CD154 blockade", *Xenotransplantation*, Vol. 9, No. 1, pp. 3-13 (2002)

[6] Cantarovich D, et al., "Rapid failure of pig islet transplantation in non human primates", *Xenotransplantation*, Vol. 9, No. 1, pp. 25-35 (2002)

[7] Carroll M C, and Fischer M B, "Complement and the immune response", *Curr Opin Immunol*, Vol. 9, No. 1, pp. 64-69 (1997)

[8] Pratt J R, et al., "Effects of complement inhibition with soluble complement receptor-1 on vascular injury and inflammation during renal allograft rejection in the rat", *Am J Pathol*, Vol. 149, No. 6, pp. 2055-2066, (1996)

[9] Fiorante P, et al., "Low molecular weight dextran sulfate prevents complement activation and delays hyperacute rejection in pig-to-human xenotransplantation models", *Xenotransplantation*, Vol. 8, No. 1, pp. 24-35, (2001)

[10] Baldwin W M, et al., "Complement in organ transplantation. Contributions to inflammation, injury, and rejection", *Transplantation*, Vol. 59, No. 6, pp. 797-808 (1995)

[11] Brauer R B, et al., "The contribution of terminal complement components to acute and hyperacute allograft rejection in the rat", *Transplantation*, Vol. 59, No. 2, pp. 288-293 (1995)

[12] Wuillemin W A, et al., "Potentiation of C1 inhibitor by glycosaminoglycans: dextran sulfate species are effective inhibitors of in vitro complement activation in plasma", *J Immunol*, Vol. 159, No. 4, pp. 1953-1960 (1997)

[13] Nakano M, et al., "Hepatocyte growth factor is essential for amelioration of hyperglycemia in streptozotocin-induced diabetic mice receiving a marginal mass of intrahepatic islet grafts", *Transplantation*, Vol. 69, No. 2, pp. 214-221 (2000)

[14] Thomas H, et al., "Sulfonated dextran inhibits complement activation and complement-dependent cytotoxicity in an in vitro model of hyperacute xenograft rejection", *Mol Immunol*, Vol. 33, No. 7-8, pp. 643-648 (1996)
[15] Korsgren O, et al., "Angiogenesis and angioarchitecture of transplanted fetal porcine islet-like cell clusters", *Transplantation*, Vol. 68, No. 11, pp. 1761-1766 (1999)
[16] Menger M D, et al., "Revascularization and microcirculation of freely grafted islets of Langerhans", *World J Surg*, Vol. 25, No. 4, pp. 509-515 (2001)
[17] Jensen R L, "Growth factor-mediated angiogenesis in the malignant progression of glial tumors: a review", *Surg Neurol*, Vol. 49, No. 2, pp. 189-195, discussion 196 (1998)
[18] Dunn I F, et al., "Growth factors in glioma angiogenesis: FGFs, PDGF, EGF, and TGFs", *Neurooncol*, Vol. 50, No. 1-2, pp. 121-137 (2000)
[19] Ricordi C, et al., "A method for the mass isolation of islets from the adult pig pancreas", *Diabetes*, Vol. 35, No. 6, pp. 649-653 (1986)
[20] Wennberg L, et al., "Diabetic rats transplanted with adult porcine islets and immunosuppressed with cyclosporine A, mycophenolate mofetil, and leflunomide remain normoglycemic for up to 100 days", *Transplantation*, Vol. 71, No. 8, pp. 1024-1033 (2001)
[21] Bradbury D A, et al., "Measurement of the ADP:ATP ratio in human leukaemic cell lines can be used as an indicator of cell viability, necrosis and apoptosis", *J Immunol Methods*, Vol. 240, No. 1-2, pp. 79-92 (2000)
[22] Wennberg L, et al., "Effects of immunosuppressive treatment on host responses against intracerebral porcine neural tissue xenografts in rats", *Transplantation*, Vol. 71, No. 12, pp. 1797-1806 (2001)
[23] Gong J, et al., "Tubing loops as a model for cardiopulmonary bypass circuits: both the biomaterial and the blood-gas phase interfaces induce complement activation in an in vitro model", *J Clin Immunol*, Vol. 16, No. 4, pp. 222-229 (1996)
[24] Sanchez J, et al., "Studies of adsorption, activation, and inhibition of factor XII on immobilized heparin", *Thromb Res*, Vol. 89, No. 1, pp. 41-50 (1998)
[25] Nilsson Ekdahl K, et al., "Generation of iC3 at the interface between blood and gas", *Scand J Immunol*, Vol. 35, No. 1, pp. 85-91 (1992)
[26] Mollnes T E, et al., "A new model for evaluation of biocompatibility: combined determination of neoepitopes in blood and on artificial surfaces demonstrates reduced complement activation by immobilization of heparin", *Artif Organs*, Vol. 19, No. 9, pp. 909-917 (1995)

The invention claimed is:

1. A method of inhibiting Instant Blood-Mediated Inflammatory Reaction (IBMIR) in a patient, comprising administering a therapeutically effective amount of dextran sulfate, or a pharmaceutically acceptable salt thereof, to a patient in need of such treatment, wherein said dextran sulfate, or said pharmaceutically acceptable salt thereof, has an average molecular weight of less than 20,000 Da and an average sulphur content in a range of 10 to 25%, and wherein inhibiting IBMIR comprises administering said therapeutically effective amount of said dextran sulfate, or said pharmaceutically acceptable salt thereof, resulting in a concentration of said dextran sulfate, or said pharmaceutically acceptable salt thereof, in the blood of said patient of less than 5 mg/ml.

2. The method according to claim 1, wherein said dextran sulfate, or said pharmaceutically acceptable salt thereof, has an average molecular weight of less than 10,000 Da.

3. The method according to claim 2, wherein said dextran sulfate, or said pharmaceutically acceptable salt thereof, has an average molecular weight of about 5,000 Da.

4. The method according to claim 1, wherein said dextran sulfate, or said pharmaceutically acceptable salt thereof, has an average sulphur content in a range of 15 to 20%.

5. The method according to claim 1, wherein inhibiting IBMIR comprises administering said therapeutically effective amount of said dextran sulfate, or said pharmaceutically acceptable salt thereof, resulting in a concentration of said dextran sulfate, or said pharmaceutically acceptable salt thereof, in said blood of said patient within a range of 0.01 mg/ml to 1.0 mg/ml.

6. The method according to claim 5, wherein inhibiting IBMIR comprises administering said therapeutically effective amount of said dextran sulfate, or said pharmaceutically acceptable salt thereof, resulting in a concentration of said dextran sulfate, or said pharmaceutically acceptable salt thereof, in said blood of said patient within a range of 0.01 mg/ml to 0.2 mg/ml.

7. The method according to claim 1, wherein inhibiting IBMIR comprises administering said dextran sulphate, or said pharmaceutically acceptable salt thereof, intravenously to said patient.

8. The method according to claim 1, wherein said patient is a diabetic patient and said cell transplant comprises isolated islets of Langerhans or isolated insulin-producing β-cells, wherein inhibiting IBMIR comprises administering said therapeutically effective amount of said dextran sulfate, or said pharmaceutically acceptable salt thereof, to inhibit IBMIR, caused by exposure of said islets of Langerhans or said insulin-producing β-cells to foreign blood of said diabetic patient following transplantation, and to achieve normoglycemia in said diabetic patient.

9. The method according to claim 1, wherein IBMIR is caused by exposure of an allogenic cell transplant or a xenogenic cell transplant, selected from a group consisting of an individual cell, a cluster of cells, or a non-vascularized tissue, to foreign blood of said patient following transplantation of said cell transplant.

10. The method according to claim 1, wherein inhibiting IBMIR comprises injecting a solution comprising said cell transplant and said dextran sulfate, or said pharmaceutically acceptable salt thereof, to said patient.

11. The method according to claim 10, wherein said dextran sulfate, or said pharmaceutically acceptable salt thereof, is administered together, in a solution, with said cell transplant to said patient and at least one time after transplantation of said cell transplant to said patient.

12. The method according to claim 10, further comprising administering said dextran sulfate, or said pharmaceutically acceptable salt thereof, once or at multiple times after transplantation of said cell transplant to said patient.

13. The method according to claim 1, wherein said patient is a diabetic patient and said cell transplant comprises isolated islets of Langerhans or isolated insulin-producing β-cells, wherein inhibiting IBMIR comprises injecting a solution comprising (i) said isolated islets of Langerhans or said isolated insulin-producing β-cells, and (ii) said dextran sulfate, or said pharmaceutically acceptable salt thereof, into a portal vein of a liver of said diabetic patient.

14. The method according to claim 1, wherein inhibiting IBMIR comprises administering said dextran sulfate, or said pharmaceutically acceptable salt thereof, prior to transplantation of said cell transplant to said patient.

15. The method according to claim 14, wherein inhibiting IBMIR comprises administering said dextran sulfate, or said pharmaceutically acceptable salt thereof, prior to transplantation of said cell transplant locally at a transplantation site of said cell transplant.

16. The method according to claim 14, where said dextran sulfate, or said pharmaceutically acceptable salt thereof, is administered prior to transplantation of said cell transplant to said patient and at least one time after transplantation of said cell transplant to said patient.

17. The method according to claim 1, wherein inhibiting IBMIR comprises administering said dextran sulfate, or said pharmaceutically acceptable salt thereof, resulting in a concentration of said dextran sulfate, or said pharmaceutically acceptable salt thereof, in the blood of said patient sufficient to (i) inhibit consumption of circulating platelets in said blood of said patient, (ii) reduce coagulation activation by decreasing the amount of factor XIa-antithrombin, factor XIIa-antithrombin, thrombin-antithrombin and plasmin-alpha 2 antiplasmin complex in said blood of said patient, and (iii) reduce complement activation by decreasing the amount of C3a fragment and soluble membrane attack complex C5b-9 in said blood of said patient.

18. A method of inhibiting morphological disruption of a transplanted cell transplant in a patient, comprising administering a therapeutically effective amount of dextran sulfate, or a pharmaceutically acceptable salt thereof, to a patient in need of such treatment, wherein said dextran sulfate, or said pharmaceutically acceptable salt thereof, has an average molecular weight of less than 20,000 Da and an average sulphur content in a range of 10 to 25%, and wherein inhibiting morphological disruption comprises administering said therapeutically effective amount of said dextran sulfate, or said pharmaceutically acceptable salt thereof, resulting in a concentration of said dextran sulfate, or said pharmaceutically acceptable salt thereof, in the blood of said patient of less than 5 mg/ml.

19. The method according to claim 18, wherein said dextran sulfate, or said pharmaceutically acceptable salt thereof, has an average molecular weight of less than 10,000 Da.

20. The method according to claim 19, wherein said dextran sulfate, or said pharmaceutically acceptable salt thereof, has an average molecular weight of about 5,000 Da.

21. The method according to claim 18, wherein said dextran sulfate, or said pharmaceutically acceptable salt thereof, has an average sulphur content in a range of 15 to 20%.

22. The method according to claim 18, wherein inhibiting said morphological disruption comprises administering said therapeutically effective amount of said dextran sulfate, or said pharmaceutically acceptable salt thereof, resulting in a concentration of said dextran sulfate, or said pharmaceutically acceptable salt thereof, in said blood of said patient within a range of 0.01 mg/ml to 1.0 mg/ml.

23. The method according to claim 22, wherein inhibiting said morphological disruption comprises administering said therapeutically effective amount of said dextran sulfate, or said pharmaceutically acceptable salt thereof, resulting in a concentration of said dextran sulfate, or said pharmaceutically acceptable salt thereof, in said blood of said patient within a range of 0.01 mg/ml to 0.2 mg/ml.

24. The method according to claim 18, wherein inhibiting said morphological disruption comprises administering said dextran sulphate, or said pharmaceutically acceptable salt thereof, intravenously to said patient.

25. The method according to claim 18, wherein inhibiting said morphological disruption comprises injecting a solution comprising said cell transplant and said dextran sulfate, or said pharmaceutically acceptable salt thereof, to said patient.

26. The method according to claim 25, further comprising administering said dextran sulfate, or said pharmaceutically acceptable salt thereof, once or at multiple times after transplantation of said cell transplant to said patient.

27. The method according to claim 18, wherein inhibiting said morphological disruption comprises administering said dextran sulfate, or said pharmaceutically acceptable salt thereof, prior to transplantation of said cell transplant to said patient.

28. The method according to claim 27, where said dextran sulfate, or said pharmaceutically acceptable salt thereof, is administered prior to transplantation of said cell transplant to said patient and at least one time after transplantation of said cell transplant to said patient.

* * * * *